United States Patent [19]

Toki et al.

[11] Patent Number: 5,218,623
[45] Date of Patent: Jun. 8, 1993

[54] METHOD AND APPARATUS FOR SPECIFYING SLICE PLANES IN X-RAY COMPUTED TOMOGRAPHY

[75] Inventors: Yusuke Toki, Utsunomiya; Makoto Hayashibara, Tochigi, both of Japan

[73] Assignee: Kabushiki Kaisha Toshiba, Kanagawa, Japan

[21] Appl. No.: 791,175

[22] Filed: Nov. 13, 1991

[30] Foreign Application Priority Data

Nov. 14, 1990 [JP] Japan .................. 2-305969

[51] Int. Cl.⁵ .......................... A61B 6/00
[52] U.S. Cl. ........................ 378/4; 378/15; 378/20
[58] Field of Search .......... 378/4, 8, 10, 15, 19, 378/20, 901, 205

[56] References Cited

U.S. PATENT DOCUMENTS

| | | |
|---|---|---|
| 4,086,492 | 4/1978 | Lodge et al. |
| 4,259,725 | 3/1981 | Andrews et al. |
| 4,649,555 | 3/1987 | Matsubayashi |
| 4,674,046 | 6/1987 | Ozeki et al. |
| 4,789,929 | 12/1988 | Nishimura et al. |
| 4,977,588 | 12/1990 | Van der Ende ............ 378/4 |
| 5,018,178 | 5/1991 | Katsumata ................. 378/4 |
| 5,023,895 | 6/1991 | McCroskey et al. ..... 378/195 |
| 5,060,246 | 10/1991 | Van der Brug et al. .... 378/20 |
| 5,084,908 | 1/1992 | Alberici et al. ............ 378/20 |
| 5,103,469 | 4/1992 | Tanaka ...................... 378/20 |

FOREIGN PATENT DOCUMENTS 2-196383 8/1990 Japan .

*Primary Examiner*—David P. Porta
*Attorney, Agent, or Firm*—Finnegan, Henderson, Farabow, Garrett & Dunner

[57] ABSTRACT

A method and an apparatus for specifying slice planes in an X-ray CT, capable of specifying a slice plane corresponding to the desired tomographic image easily and accurately. In the apparatus, scans of the body to be examined are carried out and the projection data stored in the large capacity memory first. Then, a scanogram of the body to be examined is displayed, on which a cursor is controlled in order to specify the desired slice planes corresponding to the desired tomographic images to be reconstructed. Then, the desired tomographic images are reconstructed for the desired slice planes indicated by the cursor by using an appropriate part of the projection data stored in the memory which corresponds to the desired slice planes indicated by the cursor. Either one of the helical scan and the multi-scan can be used for collecting the data to obtain the scanogram and the tomographic images.

20 Claims, 2 Drawing Sheets

METHOD AND APPARATUS FOR SPECIFYING SLICE PLANES IN X-RAY COMPUTED TOMOGRAPHY

BACKGROUND OF THE INVENTION

1. Field of the Invention

The present invention relates to an X-ray computed tomography (CT), and more particularly to a method and an apparatus for specifying slice planes for obtaining tomographic images in such an X-ray CT.

2. Description of the Background Art

In a conventional X-ray CT apparatus, in order to carry out the multi-scan imaging, the slice planes for obtaining the tomographic images are specified by selecting projection data corresponding to the desired slice planes from a list of projection data displayed on a monitor display, according to the associated data such as the table positions.

Also, in order to carry out the helical scan imaging, the projection data corresponding to the desired imaging region containing the desired slice plane are selected by using the numerical input of the table position and the number of rotations since the start of the scan.

However, in such a conventional X-ray CT apparatus in which the slice planes are specified by selecting the corresponding projection data, precisely which portions of the body to be examined are located at the specified slice planes cannot be confirmed until the reconstructed tomographic image is obtained, so that it has been difficult to accurately specify the slice plane corresponding to the desired tomographic image.

On the other hand, as disclosed in U.S. Pat. No. 4,649,555 for example, there has been a conventional X-ray CT apparatus in which the desired slice planes are specified on a scanogram of the body to be examined prior to the scanning, and then the scans are carried out in order to obtain the projection data necessary in reconstructing the tomographic images for the slice planes specified on the scanogram.

In this type of a conventional X-ray CT apparatus, because the scanning and image reconstruction are carried out after the slice planes are specified on the scanogram, it takes a considerable amount of time for the operator to inspect the reconstructed image in order to determine whether the obtained tomographic image is the desired one, i.e., if the slice planes had been specified appropriately.

Moreover, in a in which the obtained tomographic image is not the desired one, this time consuming process has to be repeated, so that it is not only time consuming but also tedious, and as a consequence there has also been a problem that the amount of X-ray irradiated on the body to be examined is increased considerably in such a case, which is potentially harmful to the body to be examined and therefore highly undesirable.

Similarly, in a case in which this type of a conventional X-ray CT apparatus is used to carry out the helical scan imaging, when the slice planes are specified on the scanogram, the apparatus is controlled by the command indicating the number of rotations before the scanning start and the number of rotations for which the scanning should continue in order to cover the specified slice planes, so that it has been necessary for the operator to inspect the reconstructed image in order to determine whether the obtained tomographic image is the desired one, i.e., if the slice planes had been specified appropriately.

Thus, just as in the case of the multi-scan imaging described above, there have been problems in the helical scan imaging case such that it can be quite time-consuming and tedious for the operator to obtain the truly desired tomographic image, and that a large amount of X-ray is irradiated on the patient.

SUMMARY OF THE INVENTION

It is therefore an object of the present invention to provide a method and an apparatus for specifying slice planes in an X-ray CT, capable of specifying slice planes corresponding to the desired tomographic images easily and accurately.

It is another object of the present invention to provide a method and an apparatus for specifying slice planes in an X-ray CT, capable of specifying slice planes corresponding to the desired tomographic images easily and accurately.

It is another object of the present invention to provide a method and an apparatus for specifying slice planes in an X-ray CT, capable of preventing the potentially harmful increase of the amount of X-ray to be irradiated on the body to be examined in a process of obtaining the desired tomographic images.

According to one aspect of the present invention there is provided an X-ray CT apparatus, comprising: scanner means including an X-ray tube and a detector for carrying out scans of a body to be examined to obtain the projection data of the body to be examined within a prescribed scanning region; memory means for storing the projection data obtained in the scans within the prescribed scanning region carried out by the scanner means; display means for displaying a scanogram of the body to be examined; cursor control means for controlling a cursor on the scanogram displayed by the display means, the cursor indicating desired slice planes corresponding to desired tomographic images; and image reconstruction means for reconstructing the desired tomographic images of the body to be examined for the desired slice planes indicated by the cursor, by using an appropriate part of the projection data stored in the memory means which corresponds to the desired slice planes indicated by the cursor.

According to another aspect of the present invention there is provided a method of X-ray CT imaging, comprising the steps of: scanning a body to be examined by using scanner means including an X-ray tube and a detector to obtain the projection data of the body to be examined within a prescribed scanning region; storing in memory means the projection data obtained by the scanner means at the scanning step; displaying a scanogram of the body to be examined on a display means; controlling a cursor on the displayed scanogram, where the cursor indicates desired slice planes corresponding to desired tomographic images; and reconstructing the desired tomographic images of the body to be examined for the desired slice planes indicated by the cursor, by using an appropriate part of the projection data stored in the memory means which corresponds to the desired slice planes indicated by the cursor.

Other features and advantages of the present invention will become apparent from the following description taken in conjunction with the accompanying drawings.

DETAILED DESCRIPTION OF THE PREFERRED EMBODIMENTS

Figure 1:
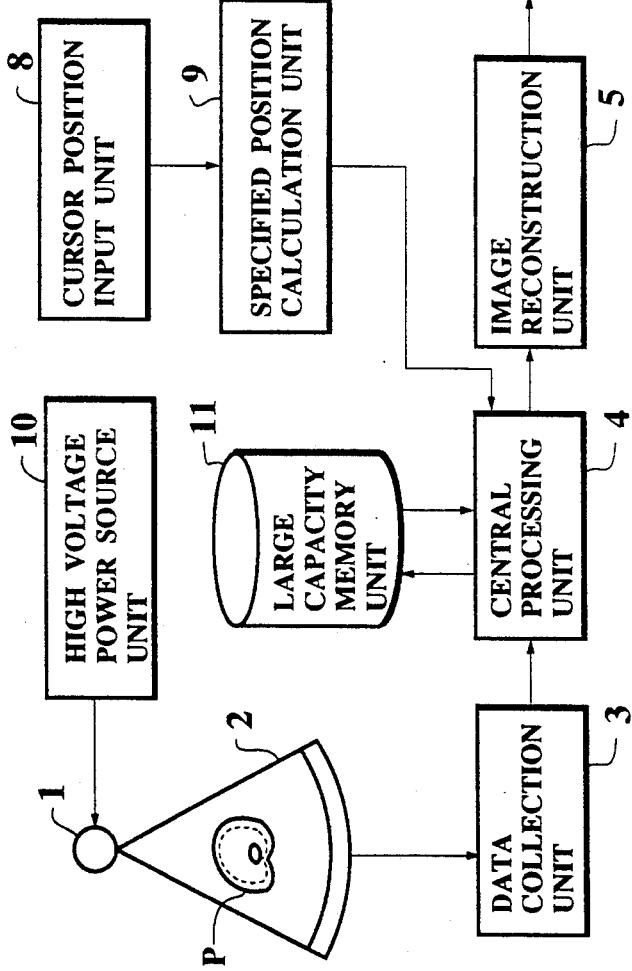
FIG. 1 is a schematic block diagram of one embodiment of an X-ray CT apparatus according to the present invention.

Referring now to FIG. 1, one embodiment of an X-ray CT apparatus according to the present invention will be described in detail.

In this embodiment, the X-ray CT apparatus comprises: an X-ray tube 1 and a detector 2 for carrying out scans with respect to a body to be examined P within a prescribed scanning region; a data collection unit 3 for collecting signals detected by the detector 2 in order to obtain projection data of the body to be examined P within the prescribed scanning region; a central processing unit 4 for controlling the operations of the apparatus as a whole; an image reconstruction unit 5 for reconstructing a scanogram and tomographic images from the projection data collected by the data collection unit 3 under the control of the central processing unit 4; an image memory 6 for temporarily storing the image which is reconstructed by the image reconstruction unit 5 and is to be displayed; a display unit 7 for displaying the image stored in the image memory unit 6; a cursor position input unit 8 for allowing an operator to specify the desired slice plane on the scanogram displayed on the display unit 7 by moving a cursor on a display screen; a specified position calculation unit 9 for calculating a position on the scanogram indicated by the cursor controlled by the operator using the cursor position input unit 8, which is fed to the central processing unit 4; a high voltage power source unit 10 for supplying high voltage power to the X-ray tube 1; and a large capacity memory unit 11 for storing projection data collected by the data collection unit 3, from which the projection data are read out under the control of the central processing unit 4 according to the position calculated by the specified position calculation unit 9 on a basis of the position of the cursor specified by the cursor position input unit 8.

In this X-ray CT apparatus, the scans by the X-ray tube 1 and the detector 2 are carried out for the prescribed scanning region first, and all the projection data obtained by the data collection unit 3 from the scans of the prescribed scanning region are stored in the large capacity memory unit 11.

Then, the scanogram is reconstructed at the image reconstruction 5 and displayed on the display unit 7. On the displayed scanogram, the operator specifies the desired slice planes for which the tomographic images are desired to be reconstructed by controlling the cursor on the scanogram.

Then, according to the desired slice planes specified on the displayed scanogram, the central processing unit 4 reads out the appropriate projection data required for reconstructing the tomographic images at the specified slice planes from the large capacity memory unit 11 and supplies these appropriate projection data to the image reconstruction unit 5, such that the desired tomographic images at the specified slice planes can be obtained by the image reconstruction unit 5.

Figure 2:
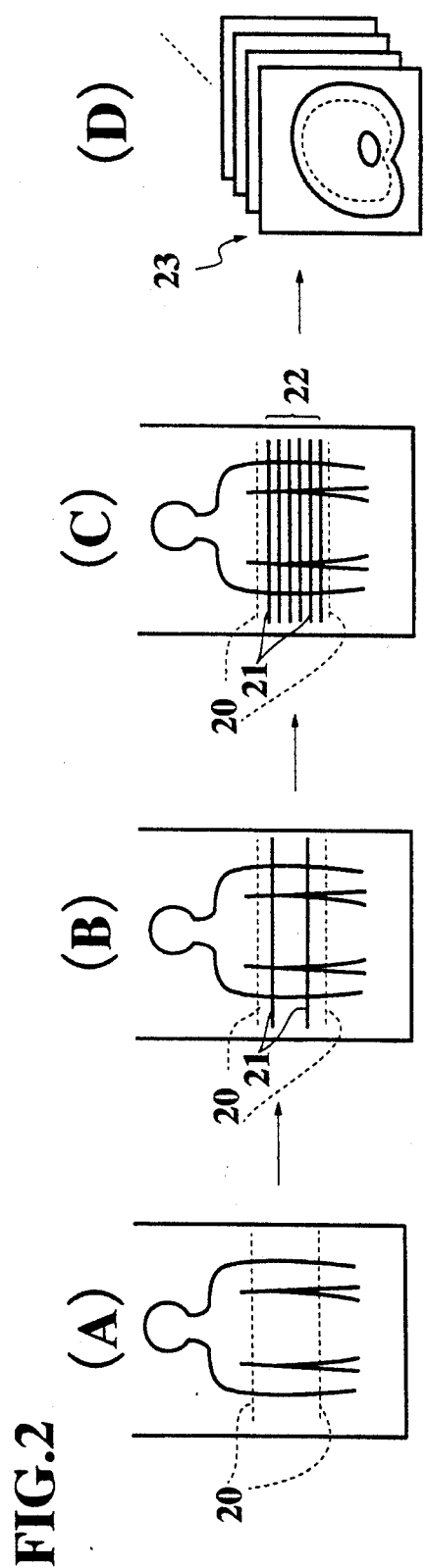
FIGS. 2A-2D are sequential illustrations of a scanogram display for specifying a slice plane in the X-ray CT apparatus of FIG. 1 in a case of helical scan imaging.

More specifically, in this X-ray CT apparatus of FIG. 1, when the helical scan imaging is to be carried out, in order to specify the desired slice plane, the central processing unit 4 controls the apparatus such that the display on the display unit 7 is sequentially changed as shown in FIG. 2.

For example, as shown in (A) of FIG. 2, the display unit 7 first displays the scanogram of the body to be examined P along with a cursor 20 indicating an image reconstructible region for which the projection data necessary in reconstructing the tomographic images have been collected by the data collection unit 3.

Then, as shown in (B) of FIG. 2, the operator is allowed to specify the slicing region including the slice planes corresponding to the desired tomographic images by using the cursor position input unit 8, such that the slicing region is indicated on the displayed scanogram by a cursor 21 located within the image reconstructible region indicated by the cursor 20.

Next, as shown in (C) of FIG. 2, the slice planes 22 for image reconstruction are displayed within the slicing region indicated by the cursor 21 on the displayed scanogram, according to the slice pitch entered by the operator through an input unit (not shown), so as to facilitate the operator's visual inspection of the slice planes for obtaining the tomographic images on the displayed scanogram in which the portions of the body to be examined P corresponding to the specified slice planes are apparent.

Then, as shown in (D) of FIG. 2, when the image reconstruction function is specified by the operator through the input unit (not shown), the image reconstruction unit 5 reconstructs the tomographic images 23 at the specified slice planes 22 by using the projection data stored in the large capacity memory unit 11 which are read out by the central processing unit 4 according to the desired slice planes specified on the displayed scanogram. The reconstructed tomographic images are subsequently displayed by the display unit 7. Here, it is to be noted that the different image reconstruction functions can be specified for the different tomographic images to be reconstructed, if necessary.

Figure 3:
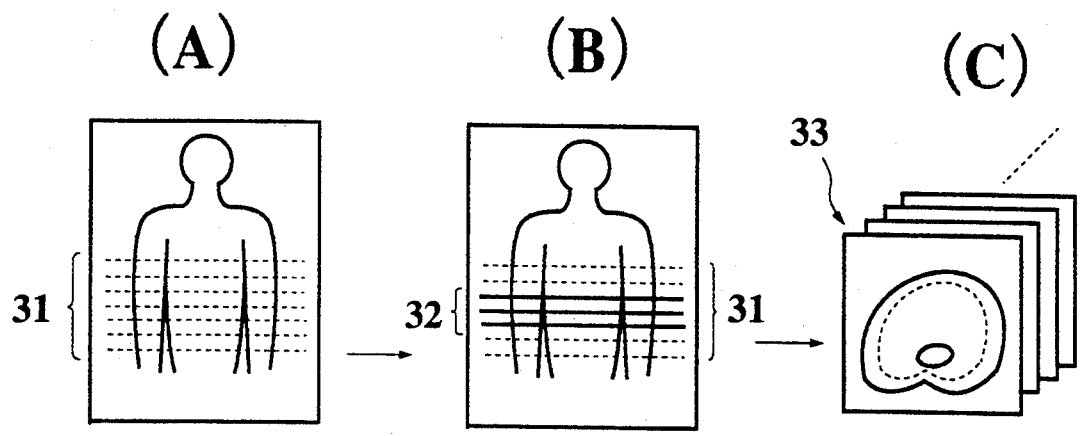
FIGS. 3A-3C are sequential illustrations of a scanogram display for specifying a slice plane in the X-ray CT apparatus of FIG. 1 in a case of multi-scan scan imaging.

On the other hand, when multi-scan imaging is to be carried out, in order to specify the desired slice plane, the central processing unit 4 controls the apparatus such that the display on the display unit 7 is sequentially changed as shown in FIG. 3.

For example, as shown in (A) of FIG. 3, the display unit 7 first displays the scanogram of the body to be examined P along with dashed lines 31 indicating slice positions at which the projection data necessary in reconstructing the tomographic images have been collected by the data collection unit 3.

Then, as shown in (B) of FIG. 3, the operator is allowed to specify the slice planes corresponding to the desired tomographic images by using the cursor position input unit 8, such that the specified slice planes are indicated on the displayed scanogram by solid lines 32 among the slice positions indicated by the dashed lines 31, so as to facilitate the operator's visual inspection of the slice planes for obtaining the tomographic images on the displayed scanogram in which the portions of the body to be examined P corresponding to the specified slice planes are apparent.

Then, as shown in (C) of FIG. 3, when the image reconstruction function is specified by the operator through the input unit (not shown), the image reconstruction unit 5 reconstructs the tomographic images 33 at the specified slice planes 32 by using the projection data stored in the large capacity memory unit 11 which are read out by the central processing unit 4 according to the desired slice planes specified on the displayed scanogram. The reconstructed tomographic images are subsequently displayed by the display unit 7. Here, it is to be noted that, just as in a case of the helical scan imaging described above, the different image reconstruction functions can be specified for the different tomographic images to be reconstructed, if necessary.

In this embodiment, in either the case of the helical scan imaging or the multi-scan imaging, the step of specifying the slice planes may be modified as follows.

Figure 4:
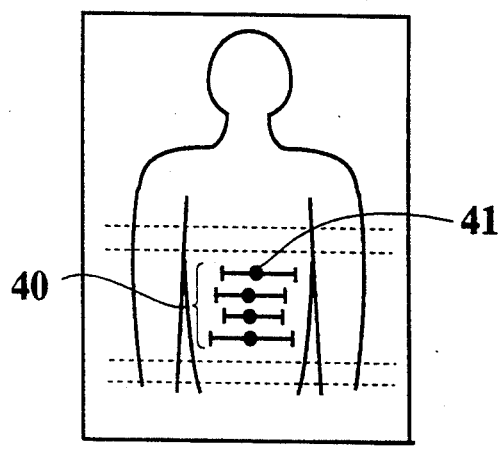
FIG. 4 is an illustration of a scanogram display for specifying the slice plane in the X-ray CT apparatus of FIG. 1, showing a possible modification to the methods of specifying a slice plane used in FIGS. 2 and 3.

As shown in FIG. 4, each of the slice planes to be set up can be indicated by a line segment 40 whose length indicates a size of the tomographic image to be reconstructed for this slice plane, and which has a center dot 41 indicating a central position of the tomographic image to be reconstructed for this slice plane, such that each tomographic image can be obtained as a zooming image of a desired area on each slice plane.

Thus, according to this embodiment, the operator can try out various possible plans for the slice planes set up, and confirm precisely which portion of the body to be examined is going to be imaged by the specified slice plane before the actual reconstruction of the tomographic images, so that it becomes possible to specify slice planes corresponding to the desired tomographic image easily and accurately.

As a consequence, the present invention is particularly useful in a case in which a large number of tomographic images are to be reconstructed.

Furthermore, according to the present invention, since the projection data for the entire scanning region are taken and stored in the large capacity memory unit before the desired slice planes are specified on the scanogram and the image is reconstructed by using the projection data stored in the large capacity memory unit, it becomes possible to specify the slice planes corresponding to the desired tomographic images easily and accurately, as well as to prevent the potentially harmful increase of the amount of X-ray to be irradiated on the body to be examined.

It is to be noted that many modifications and variations of the above embodiment may be made without departing from the novel and advantageous features of the present invention. Accordingly, all such modifications and variations are intended to be included within the scope of the appended claims.

What is claimed is:

1. An X-ray CT apparatus, comprising:
   scanner means including an X-ray tube and a detector for carrying out scans of a body to be examined to obtain the projection data of the body to be examined within a prescribed scanning region;
   memory means for storing the projection data obtained by the scans within the prescribed scanning region carried out by the scanner means;
   display means for displaying a scanogram of the body to be examined;
   cursor control means for controlling a cursor on the scanogram displayed by the display means, the cursor indicating desired slice planes corresponding to desired tomographic images; and
   image reconstruction means for reconstructing the desired tomographic images of the body to be examined for the desired slice planes indicated by the cursor, by using an appropriate part of the projection data stored in the memory means which corresponds to the desired slice planes indicated by the cursor.

2. The X-ray CT apparatus of claim 1, wherein the display means includes means for displaying the scanogram along with an indication of an image reconstructible region for which the projection data necessary for reconstructing the tomographic images are stored in the memory means, and the cursor control means includes means for controlling the cursor within the image reconstructible region.

3. The X-ray CT apparatus of claim 1, wherein the image reconstruction means includes means for reconstructing the desired tomographic images according to an externally specified image reconstruction function.

4. The X-ray CT apparatus of claim 1, wherein the scanner means includes means for carrying out a helical scan.

5. The X-ray CT apparatus of claim 4, wherein the desired scanning planes are set within a region specified by using the cursor, according to an externally specified slice pitch.

6. The X-ray CT apparatus of claim 1, wherein the scanner means includes means for carrying out a multi-scan.

7. The X-ray CT apparatus of claim 6, wherein the display means includes for displaying the scanogram along with an indication of slice positions for which the projection data necessary for reconstructing the tomographic images are stored in the memory means.

8. The X-ray CT apparatus of claim 1, wherein the display means further includes means for displaying a line segment on each of the desired slice planes, the line segment indicating a desired area to be covered by the desired tomographic image to be reconstructed by the image reconstruction means.

9. The X-ray CT apparatus of claim 8, wherein the image reconstruction means includes means for reconstructing a zoom tomographic image of the desired area indicated by the line segment for each of the desired slice planes.

10. The X-ray CT apparatus of claim 8, wherein the display means further includes means for displaying a marking on each line segment indicating a central position of the desired area indicated by the line segment.

11. A method of X-ray CT imaging, comprising the steps of:
   scanning a body to be examined by using scanner means including an X-ray tube and a detector to obtain the projection data of the body to be examined within a prescribed scanning region;
   storing in memory means the projection data obtained by the scanner means at the scanning step;
   displaying a scanogram of the body to be examined on a display means;
   controlling a cursor on the displayed scanogram, the cursor indicating desired slice planes corresponding to desired tomographic images; and reconstructing the desired tomographic images of the body to be examined for the desired slice planes indicated by the cursor, by using an appropriate part of the projection data stored in the memory means which corresponds to the desired slice planes indicated by the cursor.

12. The method of claim 11, wherein the displaying step, further includes displaying the scanogram along with an indication of an image reconstructible region for which the projection data necessary for reconstructing the tomographic images are stored in the memory means, and the controlling step further includes controlling the cursor within the image reconstructible region.

13. The method of claim 11, wherein the reconstructing step includes reconstructing the desired tomographic images according to an externally specified image reconstruction function.

14. The method of claim 11, wherein the scanning step includes carrying out a helical scan.

15. The method of claim 14, wherein the controlling step includes setting the desired scanning planes within a region specified by using the cursor, according to an externally specified slice pitch.

16. The method of claim 11, wherein the scanning step includes carrying out a multi-scan.

17. The method of claim 16, wherein the displaying step includes displaying the scanogram along with an indication of slice positions for which the projection data necessary for reconstructing the tomographic images are stored in the memory means.

18. The method of claim 11, wherein the displaying step includes displaying a line segment on each of the desired slice planes, the line segment indicating a desired area to be covered by the desired tomographic image to be reconstructed.

19. The method of claim 18, wherein the image reconstructing step includes reconstructing a zoom tomographic image of the desired area indicated by the line segment for each of the desired slice planes.

20. The method of claim 18, wherein the displaying step includes displaying a marking on each line segment indicating a central position of the desired area indicated by the line segment.

* * * * *

UNITED STATES PATENT AND TRADEMARK OFFICE
CERTIFICATE OF CORRECTION

PATENT NO. : 5,218,623
DATED : June 08, 1993
INVENTOR(S) : Yusuke TOKI et al.

It is certified that error appears in the above-indentified patent and that said Letters Patent is hereby corrected as shown below:

Claim 7, column 6, line 37, after "includes" insert --means--.

Signed and Sealed this

Twenty-ninth Day of March, 1994

Attest:

BRUCE LEHMAN

Attesting Officer

Commissioner of Patents and Trademarks